US008555876B2

(12) United States Patent  (10) Patent No.: US 8,555,876 B2
Hickle et al.  (45) Date of Patent: Oct. 15, 2013

(54) FAIL-SAFE MODULE INTEGRAL WITH A SEDATION AND ANALGESIA SYSTEM AND METHOD

(75) Inventors: Randall S. Hickle, Lubbock, TX (US); Jason Derouen, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 759 days.

(21) Appl. No.: 12/425,812

(22) Filed: Apr. 17, 2009

(65) Prior Publication Data

US 2009/0199851 A1 Aug. 13, 2009

Related U.S. Application Data

(62) Division of application No. 10/372,654, filed on Feb. 25, 2003, now Pat. No. 7,527,052.

(60) Provisional application No. 60/358,733, filed on Feb. 25, 2002.

(51) Int. Cl.
*A61M 16/10* (2006.01)
*G05B 19/048* (2006.01)

(52) U.S. Cl.
USPC ............ 128/202.22; 128/200.24; 128/203.12; 128/203.14; 128/203.15

(58) Field of Classification Search
USPC ............ 128/200.24, 202.22, 203.12, 203.25, 128/204.23, 205.11, 205.23, DIG. 12, 128/DIG. 13; 604/31, 111
See application file for complete search history.

(56) References Cited

U.S. PATENT DOCUMENTS

| | | | |
|---|---|---|---|
| 4,308,866 A | 1/1982 | Jelliffe et al. | 128/214 |
| 4,354,230 A | 10/1982 | Murphy et al. | 364/200 |
| 4,464,172 A | 8/1984 | Lichtenstein | |
| 5,016,174 A | 5/1991 | Ito et al. | 364/424.1 |
| 5,019,810 A | 5/1991 | Ito et al. | 340/825.06 |
| 5,068,853 A | 11/1991 | Soma et al. | 371/16.3 |
| 5,176,631 A | 1/1993 | Koenig | |
| 5,584,291 A | 12/1996 | Vapola et al. | |
| 5,590,648 A * | 1/1997 | Mitchell et al. | 600/301 |
| 5,628,619 A * | 5/1997 | Wilson | 417/44.2 |
| 5,651,775 A | 7/1997 | Walker et al. | 604/207 |
| 5,653,239 A | 8/1997 | Pompei et al. | 128/664 |
| 5,785,051 A | 7/1998 | Lipscher et al. | 128/207.15 |
| 5,800,361 A | 9/1998 | Rayburn | |

(Continued)

FOREIGN PATENT DOCUMENTS

| | | |
|---|---|---|
| EP | 0 840 225 A2 | 5/1998 |
| EP | 0 973 096 A2 | 1/2000 |

(Continued)

OTHER PUBLICATIONS

International Search Report dated Sep. 5, 2003, for Application No. PCT/US03/05400.

(Continued)

*Primary Examiner* — Annette Dixon
(74) *Attorney, Agent, or Firm* — Dorsey L. Baker

(57) ABSTRACT

The invention provides a fail-safe module (FSM) integral with a sedation and analgesia system that meets the high-reliability needs of sedation and/or analgesia delivered by non-anesthetist practitioners. The FSM may operate in "real-time" in order to ensure optimal patient safety. The FSM may deactivate specific patient interfaces, user interfaces, and/or sedation and analgesia delivery in order to ensure patient safety and has redundant safety systems in order to provide the fail-safe module with an accurate assessment of controller functionality.

15 Claims, 5 Drawing Sheets

(56) References Cited

U.S. PATENT DOCUMENTS

| | | | |
|---|---|---|---|
| 5,800,387 A | 9/1998 | Duffy et al. | |
| 5,807,316 A | 9/1998 | Teeple, Jr. | 604/51 |
| 5,862,394 A | 1/1999 | Watts et al. | 395/750.07 |
| 5,862,802 A | 1/1999 | Bird | |
| 5,864,291 A | 1/1999 | Walton | 340/573 |
| 5,897,596 A | 4/1999 | Kabune et al. | 701/29 |
| 6,000,396 A | 12/1999 | Melker et al. | 128/204.21 |
| 6,038,663 A | 3/2000 | Feldman | 713/1 |
| 6,200,289 B1 | 3/2001 | Hochman et al. | 604/67 |
| 6,807,965 B1 | 10/2004 | Hickle | |
| 6,829,124 B2 | 12/2004 | Leopold et al. | |
| 6,848,444 B2 * | 2/2005 | Smith et al. | 128/204.18 |
| 7,527,052 B2 | 5/2009 | Hickle | |
| 2002/0017299 A1 | 2/2002 | Hickle | |
| 2003/0029453 A1 | 2/2003 | Smith et al. | |

FOREIGN PATENT DOCUMENTS

| | | |
|---|---|---|
| JP | 4224763 | 8/1992 |
| WO | 91/03979 | 4/1991 |
| WO | 97/06844 | 2/1997 |
| WO | 98/31322 | 7/1998 |
| WO | WO 99/62403 | 12/1999 |
| WO | 00/33904 | 6/2000 |
| WO | WO 01/24690 | 12/2001 |

OTHER PUBLICATIONS

Beers., Mark H. and Rober Berkow, eds. The Merck Manual of diagnosis and Therapy. 17$^{th}$ Ed. New Jersey. Merck and Co. Inc. 1999. p. 2031, col. 2, Lines 11-16.

* cited by examiner

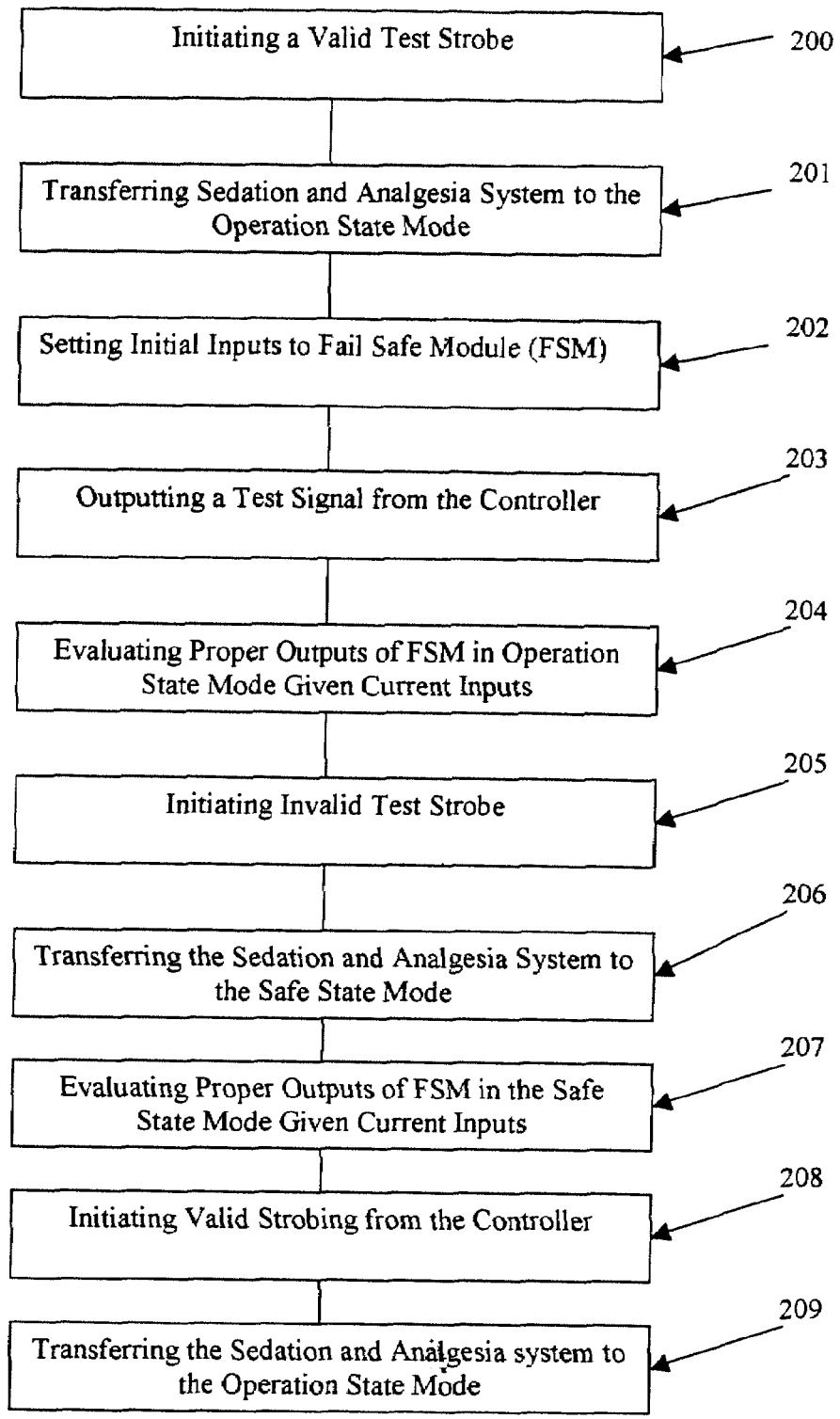

FAIL-SAFE MODULE INTEGRAL WITH A SEDATION AND ANALGESIA SYSTEM AND METHOD

CROSS REFERENCE TO RELATED APPLICATIONS

This application claims priority under 35 U.S.C. §119(e) from U.S. Provisional Patent Application No. 60/358,733, filed Feb. 25, 2002 and incorporated herein by reference. This application is also a divisional application of U.S. application Ser. No. 10/372,654, filed Feb. 25, 2003, now U.S. Pat. No. 7,527,052 issued May 5, 2009 and it also claims priority under the provisions of 35 U.S.C. 121 from the '654 application.

FIELD OF THE INVENTION

The present invention relates, in general, to fail-safe modules and, more particularly, to fail-safe modules integral with sedation and analgesia systems.

BACKGROUND OF THE INVENTION

In response to, among other things, market conditions and popularity amongst cost-conscious patients, out-of-hospital procedures continue to experience rapid growth. For various reasons, clinicians such as, for example, in office, ambulatory center, dental, non-hospital and hospital settings sometimes administer or supervise the delivery of sedation and analgesia without the services of trained anesthesia providers. This development has led the American Society of Anesthesiologists to issue guidelines for the delivery of sedation and analgesia by non-anesthesiologists. Because the non-hospital setting is in general not as well equipped and staffed as hospitals, malfunctions and complications (such as unintended over-medication leading to loss of consciousness and airway reflexes) may lead to severe outcomes.

A sedation and analgesia system is described in commonly assigned and U.S. patent application Ser. No. 09/324,759, filed Jun. 3, 1999, now U.S. Pat. No. 6,807,965. This system safely provides patients undergoing painful, uncomfortable or otherwise frightening (anxiety inspiring) medical or surgical procedures with sedative, analgesic, and/or amnestic drugs in a way that reduces the risk of overmedication, in both non-hospital and hospital settings. As this system may be used in settings where users may not be trained anesthesia providers skilled in resuscitation and airway management and where complications or malfunctions may have more severe repercussions, the number of potential failure modes was systematically reduced by elimination and/or mitigation. Mitigation was partly accomplished by careful design of the fail safe module for the sedation and analgesia system. Thus, the sedation and analgesia system may be safer than anesthesia machines for use in both non-hospital and hospital environments and may be safely operated by individuals other than trained anesthesia providers such as, for example, trained physicians, or other licensed clinicians and operators.

Anesthesia machines are mainly designed for inhalational anesthesia. In general, as a legacy from earlier anesthesia machine designs that were entirely pneumatic and did not require electrical power to operate. loss of electrical power in current anesthesia machines will not interrupt delivery of anesthetic gases and vapors. In contrast, one embodiment of the sedation and analgesia system described in the '759 application, now U.S. Pat. No. 6,807,965, uses only intravenous anesthetics and no inhalational anesthetics and requires electrical power to operate. During sedation and or analgesia, continued safety in the absence of an anesthesia provider is paramount. These safety systems often employ a set of complicated features to prevent anesthesia machines from being switched off during an anesthetic.

Existing fail-safe systems used on anesthesia machines have the ability to fall back on an all-pneumatic operation mode of operation and may not be applicable to the needs of a sedation and analgesia or total intravenous anesthesia system requiring electrical power to operate. Furthermore, because the sedation and analgesia system is also designed for use by non-anesthesia providers, the consequences of equipment failure may be more severe and thus fail safe systems with a higher reliability that those used on anesthesia machines designed for use by anesthesia providers are required.

Due to the importance of patient safety, test modes for drug delivery devices have long been accepted as an important feature. However, existing fail-safe systems may not take into account the specific requirements that the fail-safe system itself may need to be tested to attain a high-reliability sedation and analgesia system. Simulating a failure to test the fail-safe system for a sedation and analgesia system may be disruptive and cause the system to power down upon detection of the simulated failure. Upon termination of the simulated failure, if the system was powered down, the system will power up and cause further disruption, especially if the power-up, including power-up on self test (POST) routines, takes a long time to complete. Therefore, a need has arisen for a fail-safe module that may be tested without untoward system disruption, in order to confirm proper function of the fail-safe system in a high-reliability sedation and analgesia system.

Further fail-safe systems implement methods of incorporating redundant constituent elements (modules) into the systems. A further need has arisen for a watchdog system integral with a sedation and analgesia system that powers down the sedation and analgesia system in the event of a detected malfunction.

SUMMARY OF THE INVENTION

The present invention provides a fail-safe module (FSM) integral with a sedation and analgesia system that meets the high-reliability needs of sedation and/or analgesia delivered by non-anesthetists. The FSM may operate in "real-time" in order to ensure optimal patient safety. The FSM may deactivate specific patient interfaces, user interfaces, and/or sedation and analgesia delivery in order to ensure patient safety and has redundant safety systems in order to provide the fail-safe module with an accurate assessment of controller functionality.

The present invention further includes a FSM measuring the functionality of software and/or hardware associated with critical patient interfaces and/or the sedation and drug delivery system. The FSM may reactivate patient interfaces, user interfaces, and/or sedation and analgesia delivery upon receipt of acceptable data indicating an operable controller. The FSM also may retain in memory a failure event in order to alert the next user that the machine has experienced a failure. The FSM may be included with a test mode capability that simulates a failure. During the simulated failure to test the FSM, automatic system power-down may be bypassed to create minimum system disruption. The simulated failure may be programmed to occur only on power-up or during normal operation.

BRIEF DESCRIPTION OF THE DRAWINGS

FIG. 5 is a flow chart illustrating a method of operating a fail-safe test mode in accordance with the present invention.

DETAILED DESCRIPTION OF THE INVENTION

Figure 1:
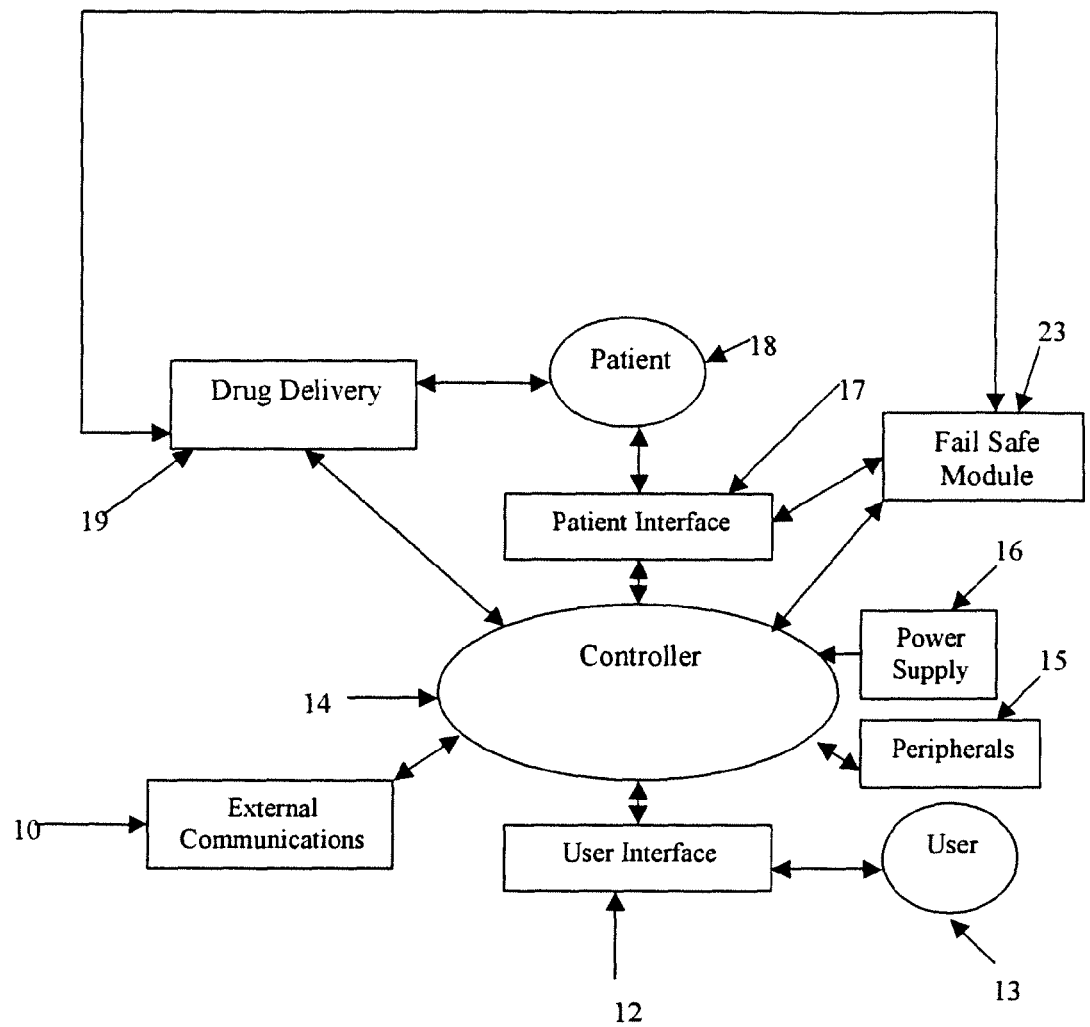
FIG. 1 is an overall conceptual schematic block diagram of a system in accordance with the present invention.

FIG. 1 illustrates a block diagram depicting one embodiment of the present invention comprising sedation and analgesia system 22 having fail-safe module 23, user interface 12, controller 14, peripherals 15 (which may include a memory device), power supply 16, external communications 10, patient interfaces 17, and drug delivery 19, where sedation and analgesia system 22 is operated by user 13 in order to provide sedation and/or drugs to patient 18. An example of sedation and analgesia system 22 is described in and commonly assigned U.S. patent application Ser. No. 09/324,759, filed Jun. 3, 1999, now U.S. Pat. No. 6,807,965, and incorporated herein by reference. Patient interfaces 17 may comprise one or more physiological monitors, such as Sp02, ECG, C02 and NIBP among others.

The sedation and analgesia system of application Ser. No. 09/324,759, now U.S. Pat. No. 6,807,965, includes a patient health monitor device (such as patient interfaces 17) adapted so as to be coupled to a patient and generate a signal reflecting at least one physiological condition of the patient, a drug delivery controller supplying one or more drugs to the patient, a memory device storing a safety data set reflecting safe and undesirable parameters of at least one monitored patient physiological condition, and an electronic controller interconnected between the patient health monitor, the drug delivery controller, and the memory device storing the safety data set; wherein said electronic controller receives said signals and in response manages the application of the drugs in accord with the safety data set.

Figure 2:
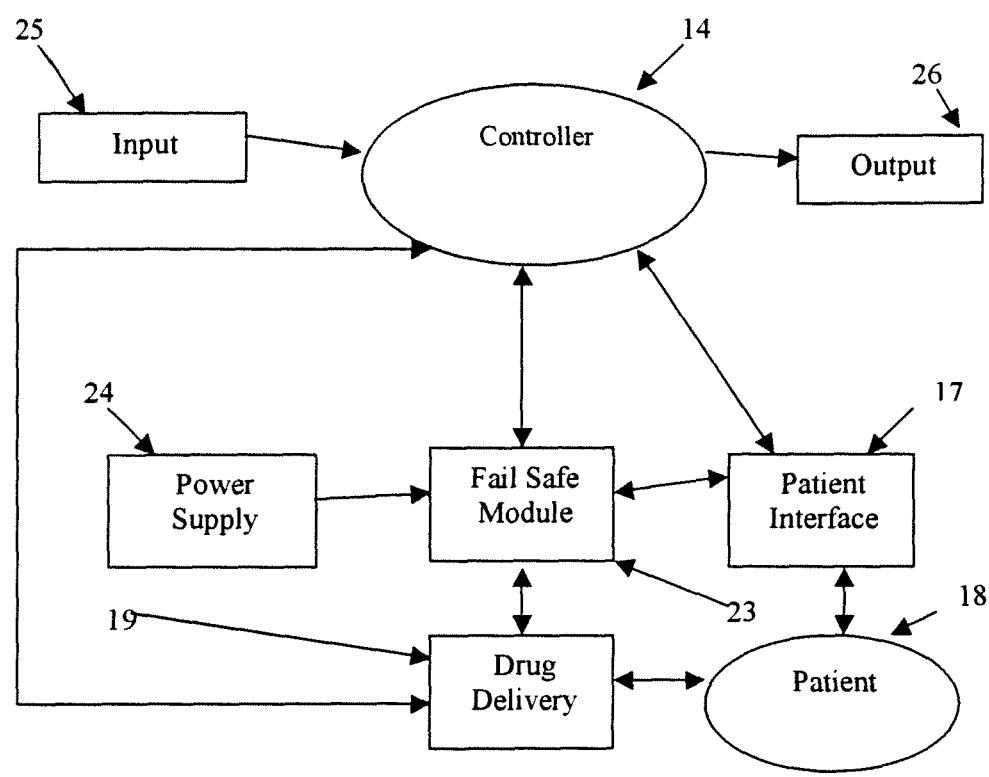
FIG. 2 is an overall schematic block diagram of a fail-safe module system in accordance with the present invention.

FIG. 2 illustrates a block diagram depicting fail-safe module system 60 having controller 14, fail-safe module 23, power supply 24, controller input 25, controller output 26, drug delivery 19, and patient interface 17, where drug delivery 19 and patient interface 17 interact with patient 18. Controller 14 receives input from patient interface 17, drug delivery 19, fail-safe module 23, and other peripherals associated with sedation and analgesia system 22. Data is inputted into controller 14 which executes a program designed in a language, such as, for example, C or C++, and functions within an operating system such as, for example, QNX. However other operating systems such as, for example, LINUX, VX Works, or Windows NT are contemplated. Preferred embodiments of the software operate in a "real time" operating system such as, for example, QNX, where programs relating to specific patient interfaces, user interfaces, and other features of sedation and analgesia system 22 are compartmentalized into separate program modules (not shown).

Controller 14 may be a CPU, or any other data processing system commonly known in the art. Controller 14 may further comprise, in one embodiment of the present invention, a health-check system (not shown) based, for example, on functionalities provided by the QNX operating system. where the health-check system sends a health check-request (not shown) to a program module (not shown) associated with a feature such as, for example, a system for the automated assessment of consciousness or responsiveness. Such an automated assessment system is described in the U.S. patent application Ser. No. 09/324,759 filed Dec. 28, 2002, now U.S. Pat. No. 6,807,965. Upon receipt of a health-check request, the program module is programmed to respond with a health check response. A malfunction of a program module will result in the failure of the module to deliver a health-check response to the health check system integral with controller 14. The health-check request and health-check response may be in the form of a single byte, a plurality of bytes, a pulse, a TTL or logic signal, or other forms of data transfer suitable for use with the present invention. If the health check system fails to receive a health check response from a program module within a given time window, controller 14 will alert fail-safe module 23 that a failure has occurred resulting in fail-safe module 23 transferring sedation and analgesia system 22 into safe state mode 107 (FIG. 4) as will be further discussed herein. The health check system is software based and exploits the inherent features of operating systems such as QNX, specifically the allocation of individual reserved memory space for each compartmentalized software program module.

In one embodiment of the present invention, data and/or commands may be outputted from controller 14 in the form of output 26 to peripherals associated with sedation and analgesia system 22, fail-safe module 23, and patient interface 17. Depending on the functionality of controller 14 and program modules associated with controller 14, controller 14 may be functioning properly, or may be outputting aberrant commands. In the event that controller 14 has malfunctioned and is outputting spurious commands and/or data, such as, for example, excessive drug delivery, fail-safe module 23 may detect improper operation in controller 14 associated with the failure and transfer sedation and analgesia system 22 into safe state mode 107 (FIG. 4).

Figure 4:
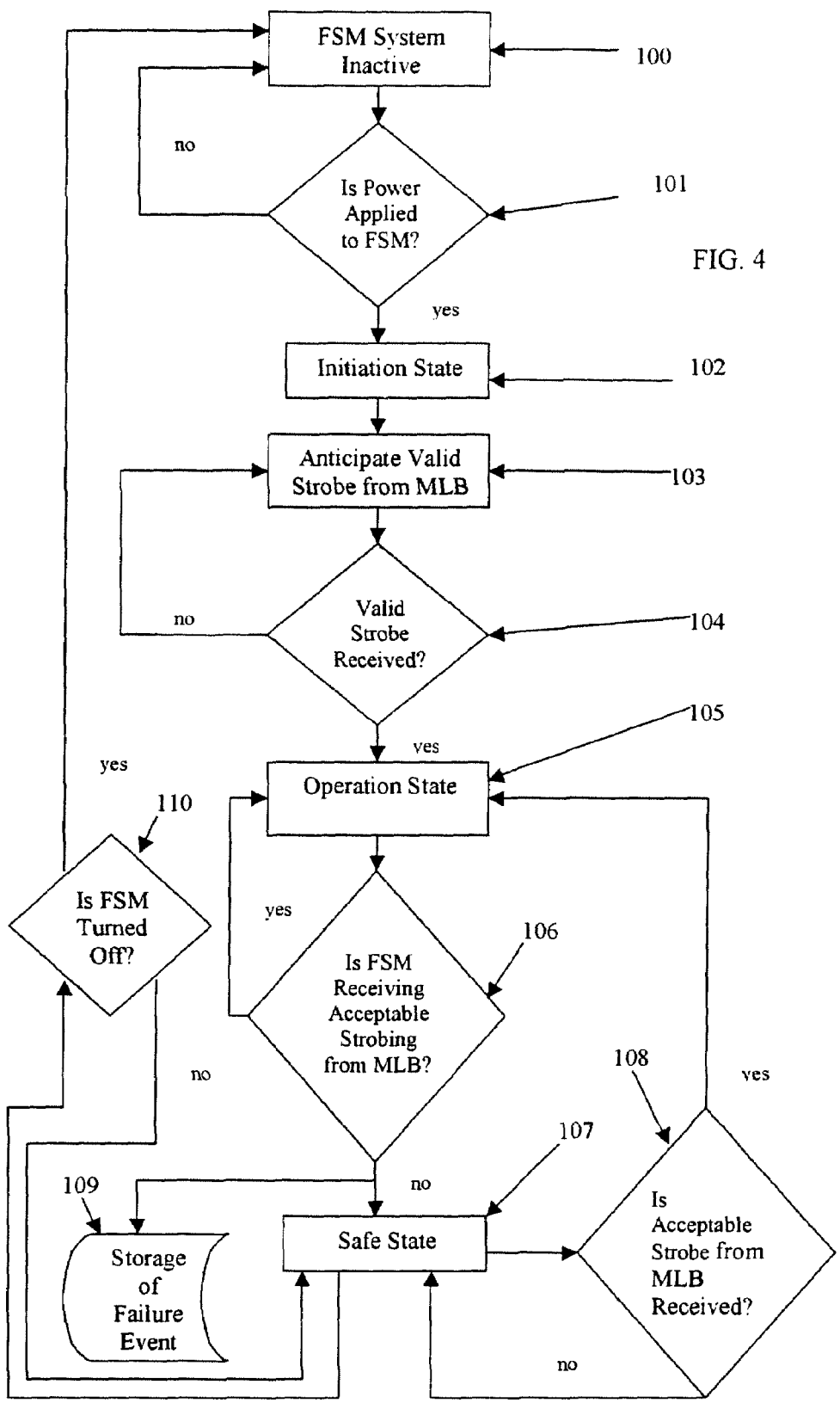
FIG. 4 is a flow chart illustrating operation of a fail-safe module system in accordance with the present invention.

In one embodiment of the present invention, controller 14 is programmed to deliver, or initiate delivery of a strobe (as shown in FIG. 4 at 103 and 104) to fail-safe system 23 within a predetermined window such as, for example, from between 900 and 1100 milliseconds. The strobe may be in the form of a byte, a plurality of bytes, a pulse, a TTL or logic signal or other forms of data transfer suitable for used with the present invention. Fail-safe module 23, in one embodiment of the present invention, must receive the strobe initiated by controller 14 within the predetermined time window in order to maintain sedation and analgesia system 22 in an operational state mode (FIG. 4). The failure of controller 14 to initiate and deliver the strobe within the specified window indicates to fail-safe module 23 that an anomaly has occurred in the health check system or in the program modules associated with sedation and analgesia systems 22, resulting in fail-safe module 123 transferring sedation and analgesia system 22 into safe state mode 107. A further embodiment of the present invention comprises providing a direct communication (not shown) between the program modules associated with sedation and analgesia system 22 and fail-safe module 23 in order to provide redundancy in verifying the program modules are functioning properly. FIG. 2 further illustrates one embodiment of the present invention, where power supply 24 is connected to and powers fail-safe module 23. In one embodiment of the present invention, power supply 24 delivers 0.5-200 volts DC and preferably 4.75-5.25 volts DC, and is capable of sourcing 0.5-200 amps and preferably 12 amps, and may be referenced to a system ground. The present invention further contemplates the use of alternating current.

Figure 3:
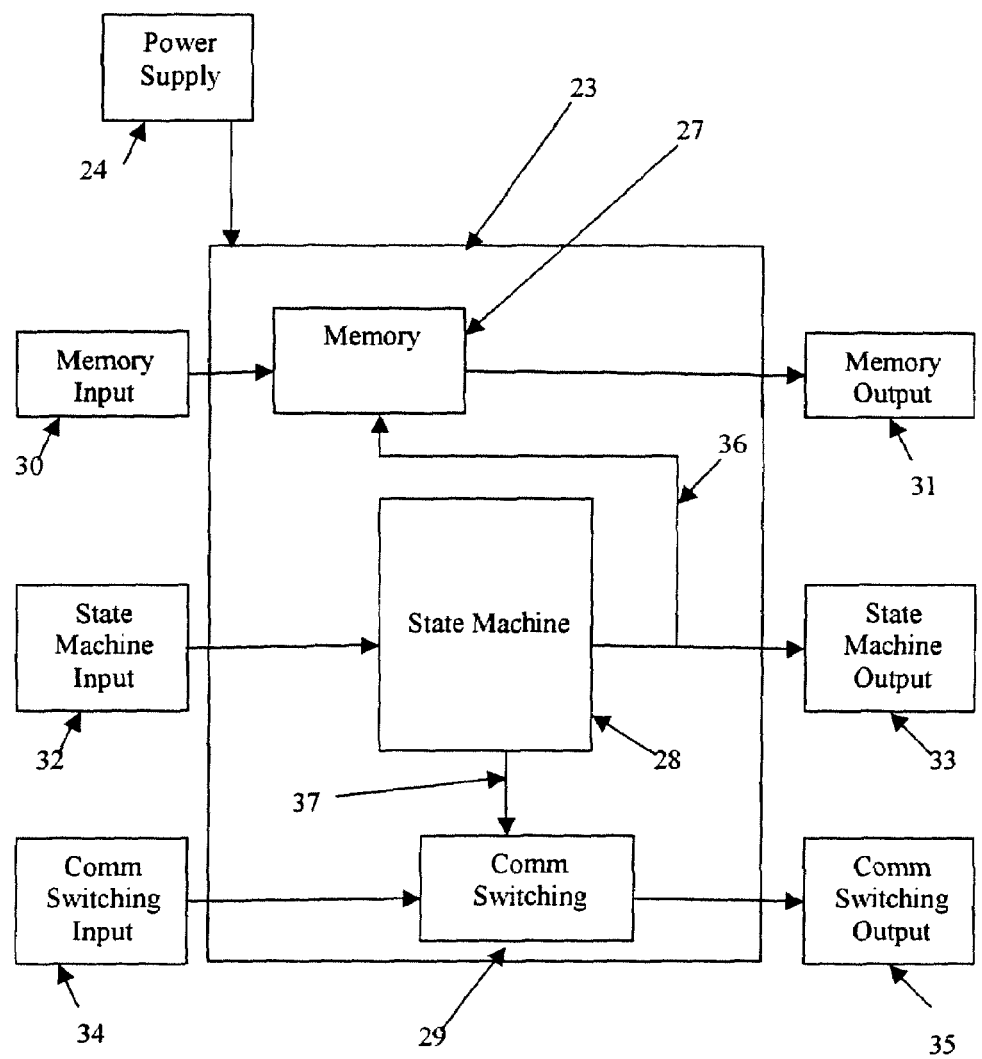
FIG. 3 is a more detailed schematic block diagram of a fail-safe module illustrating associated inputs and outputs in accordance with the present invention.

FIG. 3 illustrates a block diagram depicting one embodiment of the present invention comprising fail-safe module 23, inputs 30, 32, 34 associated with fail-safe module 23, outputs 31, 33, 35 associated with fail-safe module 23, and power supply 24. Fail-safe module 23 comprises memory 27, state machine 28, and communications (comm) switching 29. Fail-safe module 23 may be a central processing unit, a complex programmable logic device (CPLD), or any other suitable data processing device. In one embodiment of the present invention, state machine 28 receives state machine input 32, where state machine input 32 comprises a fail-safe strobe, information relevant to controlling oxygen and drug delivery, information relevant to oxygen and drug enablement, information relevant to oxygen and drug disablement, and/or other suitable state machine input. Memory 27 receives memory input 30, where memory input 30 includes, but is not limited to, information relevant to clearing fail-safe module 23 of a system fault event. Comm switching 29 receives input from comm switching input 34, where comm switching input 34 includes, but is not limited to, commands to the drug delivery module, such as among others an IV pump, from the controller 14, and commands to the non-invasive blood pressure module from controller 14. In one embodiment of the present invention, comm switching 29 functions to convert RS-232 signals to transistor logic (TTL).

Memory 27 outputs memory output 31, where memory output 31 includes, but is not limited to, information related to a failure event occurring after the last clearing of the memory 27 via memory input 30. State machine 28 outputs state machine output 33, where state machine output 33 includes, but is not limited to, an indication of an unknown system fault, output related to fail-safe module 23 control of the flowrate of oxygen and drug, and output relating to fail-safe module 23 control of enabling or disabling oxygen and drug delivery. Comm switching 29 outputs comm switching output 35, where comm switching output 35 includes, but is not limited to, information from controller 14 dictating function of the pump (not shown) associated with drug delivery 19, where the fail-safe module disables, for example, grounds, the signal if a problem is detected, and information from controller 14 dictating function of the blood pressure cuff, where the fail-safe module disables the signal if a problem is detected so that the blood pressure cuff is not left in an inflated position where it may cut off blood circulation. Routing control of oxygen delivery, the non-invasive blood pressure module (not shown), and drug delivery 19 through fail-safe module 23, allows failsafe module 23 to disable the non-invasive blood pressure module and drug delivery 19 in order to prevent potential harm to a patient due to error. Oxygen delivery may be maintained, at a predetermined flow-rate and for a predetermined period of time, by fail-safe module 23, if oxygen was being administered at the time of the failure. A plurality of other inputs and outputs, such as those described in U.S. patent application Ser. No. 09/324,759, now U.S. Pat. No. 6,807,965, are consistent with the present invention, as well as a plurality of patient interfaces such as, for example, capnometry monitoring, that may be routed through the fail-safe module 23 in order to provide desired safe state mode 107.

In one embodiment of the present invention, memory 27 functions to maintain a record of failure events occurring within controller 14 or in the program modules associated with controller 14. Information related to a failure is transmitted to memory 27 via error output path 36. Memory of the failure will be maintained within memory 27 until a command is entered acknowledging the failure and clearing the memory via memory input 30. Memory 27 functions to alert a user, via memory output 31, that sedation and analgesia system 22 has, in the previous case, experienced a failure. The recorded failure in memory 27 may be removed via memory input 30. In one embodiment of the present invention, the user may not activate the sedation and analgesia system until the failure recorded in memory 27 is acknowledged and removed. Memory of a software failure may be held in memory 27 by encoding a simple memory bit, or by other suitable means of recording a failure. One embodiment of the present invention comprises a code retained in memory 27 indicating whether the failure occurred in the program modules associated with controller 14 or in the health-check system, if the health-check system is present.

State machine 28 is, in one embodiment of the present invention, programmed to anticipate a strobe from controller 14 within a specified time window. The time window may be any window desirable for use in detecting flaws within the sedation and analgesia system 22. If the strobe is received by state machine 28 of fail-safe module 23 within the specified time window, fail-safe module 23 will maintain sedation and analgesia system 22 in operation state mode 105. If the strobe is not received by state machine 28 within the specified time window, state machine 28 will output information related to the failure via state machine output 33 in the form of a visual alarm, an audio alarm, and/or other suitable means for alerting a user that a failure has occurred. In response to a failed strobe, state machine 28 will also send data indicating a failure to memory 427 via error output path 36 and transfer sedation and analgesia system 22 into safe state mode 107. In one embodiment of the present invention, state machine 28 disables control of comm switching 29 by controller 14, via disable output 37, in order to transfer sedation and analgesia system 22 into safe state mode 107 independent of controller 14.

A further embodiment of the present invention comprises controller 14 programmed to rapidly strobe state machine 28 in the event of a failure in the modules associated with controller 14. State machine 28 is programmed, upon receipt of rapid strobing from controller 14, to output an alarm signal indicator of a sedation and analgesia system 22 failure, record the failure in memory 27, disable control of comm switching 29 by controller 14, and transfer sedation and analgesia system 22 into safe state mode 107.

FIG. 4 depicts a method illustrating one embodiment of the operation of fail-safe module 23 in this sedation and analgesia system 22. Commencing from a fail-safe module system (FSM) inactive mode 100, the sedation and analgesia system 22 only moves into initiation state mode 102 upon receipt of power (query 101) applied to fail-safe module 23. For example, initiation state mode 102 will commence upon receipt of 5 volts of direct current from power supply 24, however other voltages and means of delivering power to fail-safe module 23 are consistent with the present invention. Any time power is removed from fail-safe module 23, sedation and analgesia system 22 will return to fail-safe module system inactive mode 100. Following reception of power, sedation and analgesia system 22 will operate in an initiation state mode 102 comprising fail-safe module 23 outputting safe state output in anticipation of a strobe from controller 14. In one embodiment, fail-safe module 23 outputs safe state data until a valid strobe is received from controller 14 due to the fact that the condition of sedation and analgesia system 22 cannot be determined until valid strobing begins. Maintaining safe state output during the initiation state mode 102 ensures the controller 14 cannot send commands to important peripherals, such as, for example, drug delivery 19 or patient interface 17, until fail-safe module 23 receives a valid strobe indicating controller 14 is healthy. Initiation state mode 102 further comprises disallowing user 13 from removing the record of a failure event stored in memory 27 until a valid strobe is received from controller 14 indicating sedation and analgesia system 22 is functioning properly. In the absence of a valid strobe, sedation and analgesia system 22 will remain in initiation state mode 102. One embodiment of the present invention comprises powering down sedation and analgesia system 22 in the event that a valid strobe is not received during a predetermined window of, for example, five minutes.

Upon reception of a valid strobe from controller 14 by fail-safe module 23 (query 104), sedation and analgesia system 22 will be transferred to operation state mode 105. Operation state mode 105 is maintained contingent on valid strobing (query 106) from controller 14 to fail-safe module 23 that falls within the allowed predetermined window. Consistent valid strobing from controller 14 to fail-safe module 23 maintains sedation and analgesia system 22 in an operation state mode 105. Operation state mode 105 comprises allowing input received by fail-safe module 23 from controller 14 to control output relating to critical patient interfaces such as, for example, blood pressure cuff pressure, oxygen delivery, and drug delivery 19. Operation state mode 105 further comprises indication to user 13 that sedation and analgesia system 22 is functioning properly. Data will continue to be displayed on the user interface 12, backlighting of user interface 12 will remain active, and alarm signals relating to sedation and analgesia system 22 failure will remain quiet. One embodiment of the present invention comprises allowing user 13 or fail-safe module 23 to clear the memory unit held in memory 27 that previously indicated a failure in sedation and analgesia system 22 in order for a subsequent failure to recode the memory unit (not shown).

Failure to strobe, or rapid strobing of fail-safe module 23 (query 106) by controller 14 results in fail-safe module 23 transferring sedation and analgesia system 22 into safe state mode 107. Strobes falling outside the predetermined response window, or rapid strobing from controller 14 indicate to fail-safe module 23 that a failure has occurred in sedation and analgesia system 22. In order to protect the patient, it is necessary to convert sedation and analgesia system 22 into a safe state mode 107 to reduce potential harm caused by drug delivery 19, patient interface 17, or other critical peripherals that may include malfunctioning hardware or software. Safe state mode 107 comprises, in one embodiment of the present invention, ceasing transmission of command data from controller 14 to drug delivery 19, patient interface 17, oxygen delivery, and/or other critical peripherals related to patient safety. Safe state mode 107 further comprises deactivating drug delivery 19 in order to prevent possible patient overdose, deactivating the blood pressure cuff in order to prevent possible necrosis that occurs if the blood pressure cuff is left inflated for extended periods of time, and maintaining the flow of oxygen, if oxygen was being given during the procedure, in order to maintain suitable oxygen saturation of the blood. Safe state mode 107 further comprises triggering the memory bit located in memory 27 to indicate a sedation and analgesia system 22 failure 109, sounding an audio alarm, signaling a visual alarm, and/or blanking the display such as, for example, by deactivating the backlight on user interface 12. The backlight on user interface 12 may be deactivated in order to prevent display of spurious data that may be erroneously used to evaluate a patient's condition.

Following the transfer of sedation and analgesia system 22 to safe state mode 107, fail-safe module 23 will continue to anticipate valid strobing from the main logic board or controller 14 (query 108). Absent valid strobing, fail-safe module 23 will maintain safe state mode 107. In one embodiment of the present invention, alarms associated with fail-safe module 23 may be manually deactivated by user 13. Upon reception of a valid strobe, or a predetermined number of valid strobes from controller 14, fail-safe module 23 may transfer sedation and analgesia system 22 from safe state mode 107 to operation state mode 105. A further embodiment of the present invention comprises sedation and analgesia system 22 remaining in safe-state mode for the duration of the medical procedure, even in the event of a valid strobe from controller 14.

Query 110 relates to user 13 response to safe state mode 107. If sedation and analgesia system 22 is turned off, sedation and analgesia system 22 will be transferred to fail-safe module inactive mode 100. If sedation and analgesia system 22 is not deactivated, fail-safe module 23 will maintain sedation and analgesia system 22 in safe state mode 107.

FIG. 5 depicts a method illustrating one embodiment of a test mode 210 for sedation and analgesia system 22 comprising the steps of: initiating a valid test strobe 200, transferring sedation and analgesia system to the operation state mode 201, setting inputs to the FSM 202, outputting a test signal from the controller 203, evaluating proper outputs of FSM in operation state mode given current inputs 204, initiating valid test strobe 205, transferring the sedation and analgesia system to the safe state mode 206, evaluating proper outputs of FSM in safe state mode given current inputs 207, initiating valid strobing from the controller 208, and transferring the fail-safe module to the operation state mode 209.

In one embodiment of the present invention, initiating a valid test strobe step 200 comprises transmitting one or a plurality of strobes from controller 14 to fail-safe module 23 that fall into the predetermined time window programmed into fail-safe module 23, indicating that controller 14 is functioning properly. In one embodiment of the present invention, initiating a valid test strobe step 200 occurs during initiation state mode 102 after power has been delivered to controller 14 and fail-safe module 23.

Transferring sedation and analgesia system to the operation state mode step 201 comprises, fail-safe module 23 receiving the valid strobe or strobes from controller 14, where the valid strobe or strobes indicate to fail-safe module 23 that controller 14 is functioning properly, then converting sedation and analgesia system 22 to operation state mode 105 based on the valid strobe or strobes indicating that sedation and analgesia system 22 is functioning properly.

Setting initial inputs to FSM step 202 comprises inputting information related to oxygen delivery, drug delivery 19, patient interface 17, or other critical parameters relating to a desired safe state mode 107. In one embodiment of the present invention, setting initial inputs to FSM step 202 occurs during operation state mode 105, where controller 14 maintains control of critical parameters.

Outputting a test signal from the controller (step 203) comprises, user 13 inputting a test command into controller 14, where the inputted test command decouples the power down functionality from detected failure of sedation and analgesia system 22. One embodiment of the present invention comprises an automated system of initiating a test command, where the test command is initiated by controller 14 at a predetermined time before the beginning of a medical procedure, for example as part of the power-up routine of a sedation and analgesia system. In one embodiment of the present invention, a test bit (not shown) is triggered in fail-safe module 23 upon receipt of the test command from controller 14. The triggered test bit of fail-safe module 23 may function to disable the power down capability associated with a failure, in order to test the functionality of fail-safe module 23 without initiating a power down. Providing a FSM test mode, absent a power down, obviates the need to retest fail-safe module 23 following a subsequent power up of the system had the system been powered down as part of the simulated failure.

Evaluating proper outputs of the FSM in the operation state mode given current inputs (step 204) comprises determining whether fail-safe module 23 is outputting data consistent with inputted data. In evaluating proper outputs of the FSM in the operation state mode given current inputs (step 204), outputted data should be consistent with inputted data due to the retention of control of critical parameters associated with fail-safe module 23 by controller 14.

Initiating invalid test strobe (step 205) comprises outputting an invalid strobe from controller 14 to fail-safe module 23, simulating a failure of sedation and analgesia system 22. The invalid test strobe may be rapid strobing of fail-safe module 23 by controller 14, strobing outside the predetermined time window, or other suitable means of communicating a failure of sedation and analgesia system 22.

Transferring the sedation and analgesia system to the safe state mode step 206 comprises transferring sedation and analgesia system 22 to safe state mode 107 following receipt by fail-safe module 23 of an invalid strobe. In order to prevent the need for repetitive retesting upon power up of sedation and analgesia system 22 were it to be powered down during the simulated failure, sedation and analgesia system 22 is not powered down during test mode 210.

Evaluating proper outputs of the FSM in the safe state mode given current inputs (step 207) comprises determining whether fail-safe module 23 is functioning properly in converting sedation and analgesia system 22 to safe state mode 107. Evaluating proper outputs of the FSM in the safe state mode given current inputs (step 207) allows controller 14 to determine if fail-safe module 23 will function properly, in the event of an actual failure, in converting sedation and analgesia system 22 to safe state mode 107.

Initiating valid strobing from the controller step 208 comprises outputting a valid strobe or strobes from controller 14 to fail-safe module 23 following the transfer of sedation and analgesia system to safe state mode 107. Upon receipt of valid strobing, that is, strobing falls within the predetermined response window, fail-safe module 23 will transfer sedation and analgesia system 22 to operation state mode 105, reallocating control of drug delivery system 19, patient interface 17, and oxygen delivery to controller 14. Transfer of sedation and analgesia system 22 from safe state mode 107 to operation state mode 105 following successful strobing is consistent with transferring the sedation and analgesia system to the operation state mode (step 209).

Test mode 210 provides user 13 with a simulation of a failure event or message, where the response of fail-safe module 23 may be tested, in the absence of a power down, to determine whether it functions properly in transferring sedation and analgesia system 22 to safe state mode 107 and operation state mode 105 at the appropriate times. The memory bit recorded in memory 27 of the fail-safe module 23 may be reset upon transfer of sedation and analgesia system 22 to operation state mode 105.

In one embodiment of the invention, the health check system polls each compartmentalized software module and verifies that each one indicates that it is operating properly. Upon receipt from all compartmentalized software modules that all is well, the health check system strobes the FSM to indicate that all system modules are functioning properly. This health check system occurs at all times that the system is running. The health check system is software based and the FSM is implemented via hardware such as a complex programmable logic device (CPLD).

The invention claimed is:

1. A method of safely operating a sedation and analgesia system, wherein the system comprises an electronic controller connected to a fail safe module, to one or more patient interfaces for monitoring the physiological condition of the patient during a medical procedure and to a drug delivery device and wherein the controller monitors the one or more patient interfaces during the operation of the system to confirm a safe physiological condition of the patient, and to control the drug delivery device, the method comprising the steps of:

applying power to said system and commencing the operation of the fail safe module to operate said system in a safe state mode in which drug delivery is disabled, and upon receiving one or more valid signals indicating proper operation of the controller, enabling control of the system by said controller;

electronically managing the delivery of pain or anxiety relieving drugs to a patient and monitoring the operation of the one or more patient interfaces with the controller; and monitoring the proper operation of the controller with said fail safe module and, in the event of improper operation of said controller, returning said system to said safe state mode of operation.

2. The method of safely operating a sedation and analgesia system according to claim 1, wherein a user interface indicates the system is not functioning properly.

3. The method of safely operating a sedation and analgesia system according to claim 1, wherein the user interface indicates the system is not functioning properly with one or more system state alarms.

4. The method of safely operating a sedation and analgesia system according to claim 1, further comprising the step of powering down the sedation and analgesia system upon the non-receipt by the fail safe module of the one or more valid signals indicating a healthy proper operation of the controller.

5. The method of safely operating a sedation and analgesia system according to claim 1, wherein the fail safe comprises memory, and wherein the fail safe module retains in its memory a signifier upon the non-receipt by the fail safe module of the one or more valid signals indicating proper operation of the controller.

6. The method of safely operating a sedation and analgesia system according to claim 1, wherein the one or more valid signals comprise a strobe delivered or initiated by the controller for receipt by the fail safe module.

7. The method of safely operating a sedation and analgesia system according to claim 6, wherein the strobe is an electrical strobe in the form of a byte, a plurality of bytes, a pulse, or logic signal.

8. The method of safely operating a sedation and analgesia system according to claim 1, further comprising the step of testing the fail safe module prior to the step of commencing operation of the sedation and analgesia system.

9. The method of safely operating a sedation and analgesia system according to claim 8, wherein the steps of initiating a valid test strobe comprises transmitting one strobe or a plurality of strobes from the controller to the fail safe module that fall into a predetermined time window programmed into the fail safe module, wherein such strobe or strobes indicate that the controller is functioning properly.

10. The method of safely operating a sedation and analgesia system according to claim 8, wherein the steps of initiating an invalid test strobe comprises outputting an invalid strobe from the controller to the fail safe module to simulate a failure of the sedation and analgesia system.

11. The method of safely operating a sedation and analgesia system according to claim 8, wherein the invalid strobe comprises rapid strobing or strobing outside of a predetermined time window.

12. A method of safely operating a sedation and analgesia system for delivering a sedative and/or analgesic drug to a patient during a medical and/or surgical procedure, wherein the system comprises an electronic controller, one or more patient interfaces for monitoring the physiological condition of the patient, a drug delivery device and a fail safe module and wherein the controller receives input from the one or more patient interfaces during the operation of the system to confirm that the patient is in a safe physiological condition, the method comprising the steps of:

commencing the operation of the fail safe module comprising the step of the fail safe module outputting safe state data in which drug delivery is disabled until a valid strobe or strobing is received from the controller;

upon reception by the fail safe module of the valid strobe or strobing from the controller, commencing the operation of the sedation and analgesia system;

electronically managing the delivery of the drug delivery device by the controller;

providing signals from said controller to said fail safe device to indicate proper functioning of said controller and a safe physiological condition of the patient, and returning said system to said safe state mode in the event of improper functioning of said controller.

13. The method of safely operating a sedation and analgesia system according to claim 12, wherein the operation of the fail safe module further comprises resumption of said safe state data output upon receipt of a valid strobe or strobing from the controller.

14. The method of safely operating a sedation and analgesia system according to claim 12, wherein the operation of the fail safe module further comprises transferring the sedation and analgesia system into a safe state mode upon non-receipt of valid strobe or strobing from the controller.

15. The method of safely operating a sedation and analgesia system according to claim 14, wherein upon receipt of a valid strobe or strobing from the controller, the fail safe module recommences operation of the sedation and analgesia system.

* * * * *